(12) United States Patent
Agarwal et al.

(10) Patent No.: US 6,869,441 B2
(45) Date of Patent: Mar. 22, 2005

(54) THERMAL THERAPY SLEEVE

(75) Inventors: Naveen Agarwal, Evansville, IN (US); Jeffrey E. Fish, Dacula, GA (US); Ilona F. Weart, Woodstock, GA (US); Jeffrey M. Willis, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 178 days.

(21) Appl. No.: 10/394,782

(22) Filed: Mar. 21, 2003

(65) Prior Publication Data

US 2004/0186541 A1 Sep. 23, 2004

(51) Int. Cl.⁷ .................................................. A61F 7/00
(52) U.S. Cl. ...................................... 607/114; 62/457.2
(58) Field of Search ........................... 607/96, 108–112, 607/114; 62/371, 457.2

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,763 A | 3/1970 | Hartmann |
| 3,542,615 A | 11/1970 | Dobo et al. |
| 3,643,665 A | 2/1972 | Caillouette |
| 3,674,134 A | 7/1972 | Turner |
| 3,692,618 A | 9/1972 | Dorschner et al. |
| 3,763,622 A | 10/1973 | Stanley, Jr. |
| 3,802,817 A | 4/1974 | Matsuki et al. |
| 3,804,077 A | 4/1974 | Williams |
| 3,849,241 A | 11/1974 | Butin et al. |
| 3,865,117 A | 2/1975 | Perry, III |
| 3,874,504 A | 4/1975 | Verakas |
| 4,041,203 A | 8/1977 | Brock et al. |
| 4,100,324 A | 7/1978 | Anderson et al. |
| 4,340,563 A | 7/1982 | Appel et al. |
| 4,451,383 A | 5/1984 | Arrhenius |
| 4,462,224 A | 7/1984 | Dunshee et al. |
| 4,756,958 A | 7/1988 | Bryant et al. |
| 4,793,323 A | 12/1988 | Guida et al. |
| 4,818,464 A | 4/1989 | Lau |
| 4,856,294 A | 8/1989 | Scaringe et al. |
| 4,871,615 A | 10/1989 | Vigo et al. |
| 4,886,063 A | 12/1989 | Crews |
| 4,964,402 A | 10/1990 | Grim et al. |
| 4,995,217 A | 2/1991 | Francis, Jr. |
| 5,106,520 A | 4/1992 | Salyer |
| 5,145,727 A | 9/1992 | Potts et al. |
| 5,169,706 A | 12/1992 | Collier et al. |
| 5,178,931 A | 1/1993 | Perkins et al. |
| 5,188,885 A | 2/1993 | Timmons et al. |
| 5,211,949 A | 5/1993 | Salyer |
| 5,237,838 A * | 8/1993 | Merritt-Munson ......... 62/457.2 |
| 5,254,380 A | 10/1993 | Salyer |

(List continued on next page.)

FOREIGN PATENT DOCUMENTS

| | | |
|---|---|---|
| WO | WO 01/39704 A1 | 6/2001 |
| WO | 01/60298 A2 | 8/2001 |
| WO | 01/60305 A1 | 8/2001 |

Primary Examiner—Roy D. Gibson
(74) Attorney, Agent, or Firm—Dana E. Stano

(57) ABSTRACT

A flexible thermal therapy sleeve is disclosed. The sleeve includes a first layer including a first phase change material having a transition temperature of from about −10° C. to about 40° C., and a second layer including a second phase change material having a transition temperature of from about 35° C. to about 65° C. The first layer is joined to the second layer to form at least a partial enclosure having an opening through which a thermoactive material may be inserted and removed.

20 Claims, 14 Drawing Sheets

U.S. PATENT DOCUMENTS

| | | | |
|---|---|---|---|
| 5,282,994 A | 2/1994 | Salyer | |
| 5,366,801 A | 11/1994 | Bryant et al. | |
| 5,415,222 A | 5/1995 | Colvin et al. | |
| 5,423,996 A | 6/1995 | Salyer | |
| 5,499,460 A | 3/1996 | Bryant et al. | |
| 5,534,020 A | 7/1996 | Cheney, III et al. | |
| 5,545,197 A * | 8/1996 | Bowen | 607/108 |
| 5,552,075 A | 9/1996 | Salyer | |
| 5,637,389 A | 6/1997 | Colvin et al. | |
| 5,650,090 A | 7/1997 | Salyer | |
| 5,722,482 A | 3/1998 | Buckley | |
| 5,800,491 A | 9/1998 | Kolen et al. | |
| 5,899,088 A * | 5/1999 | Purdum | 62/371 |
| 5,935,157 A | 8/1999 | Harmon | |
| 6,004,662 A | 12/1999 | Buckley | |
| 6,099,555 A | 8/2000 | Sabin | |
| 6,132,455 A | 10/2000 | Shang | |
| 6,183,855 B1 | 2/2001 | Buckley | |
| 6,217,993 B1 * | 4/2001 | Pause | 428/218 |
| 6,233,945 B1 | 5/2001 | Kohout | |
| 6,251,131 B1 | 6/2001 | Kohout | |
| 6,302,902 B1 | 10/2001 | Benja-Athon | |
| 6,319,599 B1 | 11/2001 | Buckley | |
| 6,422,032 B1 * | 7/2002 | Greene | 62/457.2 |
| 2002/0054964 A1 | 5/2002 | Hartmann | |

\* cited by examiner

THERMAL THERAPY SLEEVE

BACKGROUND OF THE INVENTION

The use of cold or heat therapy has long been known in the medical field. Cold therapy may be used to treat certain limb injuries, such as sprained or strained arm or leg muscles, or injuries to joints. Generally, cold may be applied to these types of injuries to slow blood flow, which reduces swelling, pain, and further damage. Heat therapy may be used to warm or limber muscles by increasing blood flow. For example, athletes may apply heat to thighs or calf muscles prior to an athletic event. In another application, a small chemical heat pack commonly referred to as a "heel warmer" is activated and placed against the foot of a newborn infant to increase the infant's blood flow prior to drawing a blood sample.

A number of products may be used to provide heat or cold therapy. For example, chemical heat or cold products involve a bag or pack containing two or more reagents separated by a membrane. When the user ruptures the membrane, the reagents mix and undergo either an exothermic or endothermic reaction. This type of product provides the user instant heat or cold. When the heating or cooling effect subsides, the product is disposed of. Other thermal therapy products, for example, gel-based hot or cold packs, are reusable but require the user to supply external energy before use, e.g., heat from a microwave oven or cold from a freezer. These products are often less effective than instant chemical hot or cold packs because they are unable to maintain the desired minimum or maximum temperature.

The thermal therapy techniques of the prior art present two challenges. First, many disposable thermal therapy products, while convenient, are unable to deliver or absorb heat for an extended duration. Second, many existing thermal therapy products cause temperature spikes that may result in discomfort to the user, while others are unable to attain the desired therapeutic temperature. Thus, there is a need for a device that provides an extended therapeutic benefit at the desired temperature while eliminating undesirable temperature peaks.

SUMMARY OF THE INVENTION

The present invention relates to a flexible thermal therapy sleeve that extends the therapeutic duration of a thermoactive material. The sleeve may include a first layer including a first phase change material having a transition temperature of from about −10° C. to about 40° C., and a second layer including a second phase change material having a transition temperature of from about 35° C. to about 65° C. The first layer may be joined to the second layer to form at least a partial enclosure having an opening through which a thermoactive material may be inserted and removed. In some embodiments, the first phase change material may be n-eicosane, n-hemeicosane, n-docosane, n-tricosane, n-tetracosane, n-pentacosane, n-hexacosane, n-heptacosane, n-octacosane, or combinations thereof. In some embodiments, the second phase change material may be n-tridecane, n-tetradecane, n-pentadecane, n-hexadecane, n-heptadecane, n-octadecane, n-nonadecane, n-eicosane, or combinations thereof.

The present invention further relates to a flexible thermal therapy sleeve that may include a first layer including a first phase change material and a second phase change material, where the first phase change material may have a transition temperature of from about −10° C. to about 40° C. and the second phase change material may have a transition temperature of from about 35° C. to about 65° C. The sleeve may further include a second layer joined to the first layer to form at least a partial enclosure having an opening through which a thermoactive material may be inserted and removed. In some embodiments, the second layer may include a third phase change material.

The present invention also relates to a thermal therapy system having an extended therapeutic duration. The system may include a thermoactive material such as a chemical pack, where the pack may include a first phase change material, a solute, and a solvent. In some embodiments, the solute and the solvent may be separated by a membrane, and the rupturing of the membrane causes the combination of the solute and solvent and produces an endothermic reaction or an exothermic reaction. The system may further include a flexible sleeve having a first layer and a second layer, the first layer including a second phase change material having a transition temperature of from about −10° C. to about 40° C. and a third phase change material having a transition temperature of from about 35° C. to about 65° C. The second layer may be joined to the first layer to form at least a partial enclosure having an opening through which the thermoactive material may be inserted and removed. Any suitable solute and solvent may be used, and in some embodiments, the solute may be ammonium nitrate or calcium chloride.

The present invention finally contemplates a thermal therapy system having an extended therapeutic duration that may include a thermoactive material such as a chemical pack. The pack may include a first phase change material, a solute, and a solvent, where the solute and the solvent are separated by a membrane, and where the rupturing of the membrane causes the combination of the solute and solvent and produces an endothermic reaction or an exothermic reaction. The system may also include a flexible sleeve having a first layer and a second layer, where the first layer may include a second phase change material having a transition temperature of from about −10° C. to about 40° C., and the second layer may include a third phase change material having a transition temperature of from about 35° C. to about 65° C. The first layer may be joined to the second layer to form at least a partial enclosure having an opening through which the thermoactive material may be inserted and removed. Any suitable phase change materials may be used, and in some embodiments, the first phase change material, the second phase change material, and the third phase change material may be n-eicosane, n-hemeicosane, n-docosane, n-tricosane, n-tetracosane, n-pentacosane, n-hexacosane, n-heptacosane, n-octacosane, n-tridecane, n-tetradecane, n-pentadecane, n-hexadecane, n-heptadecane, n-octadecane, n-nonadecane, n-eicosane, or a combination thereof.

DESCRIPTION OF THE INVENTION

Figure 1:
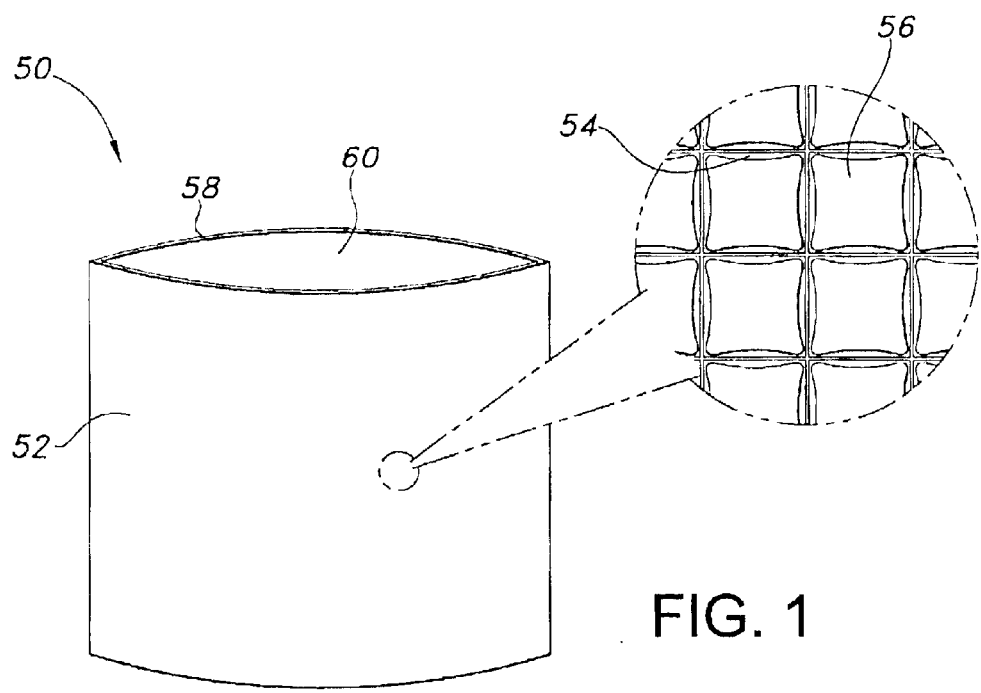
FIG. 1 depicts an exemplary thermal therapy sleeve for use with the present invention, where a layer of the sleeve includes hollow chambers containing a phase change material.

The present invention relates to a thermal therapy system that features an extended therapeutic life. The extended life is attributed to use of at least one phase change material (PCM) in cooperation with traditional thermal therapy techniques. In particular, the PCM is incorporated into a thermal therapy sleeve into which a thermoactive material is inserted. A "thermoactive material" is any substance that is able to provide or absorb heat at room temperature, or multiple substances that generate or absorb heat when combined by, for example, an exothermic reaction or endothermic reaction, respectively. Thermoactive materials include, for example, ice, gels, chemical reagents such as salts and water, and the like. Thermoactive materials may be provided in a package or may otherwise be contained for user convenience. For instance, many thermoactive materials are incorporated into instant chemical hot or cold packs, commercially available gel packs, metal oxidation products, and the like, also referred to as "thermal therapy products" herein. More particularly, a "cold therapy product" refers to a product that consumes heat and provides a cooling effect, and a "heat therapy product" refers to a product that generates or emits heat and provides a warming effect.

The thermal therapy system of the present invention overcomes the deficiencies of the prior art by providing a flexible, reusable thermal therapy sleeve sized to accommodate a thermoactive material. The sleeve contains a PCM that may be regenerated by simply replacing the spent thermoactive material, for example, a thermal therapy product such as a chemical or gel-based hot or cold pack. By doing so, the duration of the thermal therapy is extended. This presents a significant advantage over current products that require inconvenient and time-consuming external regeneration using an independent energy source, such as placement in a cool (e.g. freezer) or warm (e.g. microwave) environment for a lengthy period of time prior to reuse.

The PCM may be incorporated into the sleeve in a variety of manners, such as, for example, by including it in hollow chambers within a layer of the sleeve, by co-extruding it with fibers that form a layer of the sleeve, or by integrating an encapsulated form of the PCM into the fibrous matrix of a layer of the sleeve.

The present invention also relates to a method of extending the therapeutic life of a thermal therapy product. In general, a traditional thermal therapy product may be used with the thermal therapy sleeve of the present invention to both modulate the temperature of the traditional product and extend the therapeutic duration of the product.

To better understand what is contemplated by the present invention, a more detailed description is provided below.

A material typically consumes or releases thermal energy in proportion to its heat capacity, which varies as a function of temperature. The variation in heat capacity is small if the material does not undergo a phase transition within the temperature range of interest. There is, however, a nonlinear change in heat capacity at or around the temperature of phase change, i.e., the transition temperature, that typically allows a much larger amount of thermal energy to be either consumed by or released from the material as the material melts or freezes, respectively.

Phase change materials (PCM's) are materials that are able to undergo a reversible phase transition at a precise temperature. Common PCM's include, for example, low molecular weight aliphatic hydrocarbons, paraffin waxes, and acids of natural oils and waxes. Paraffinic hydrocarbons are well-suited for attaining the desired temperature for a given thermal therapy application because there is a fairly strong correlation between the number of carbon atoms in the hydrocarbon and its melting point. Thus, for a given application, the desired therapeutic temperature may readily be attained by selection of the appropriate PCM or combination of PCM's. Various exemplary paraffinic hydrocarbons are listed below.

| Compound | Carbon atoms | Transition temperature (° C.) |
| --- | --- | --- |
| n-Octacosane | 28 | 61.4 |
| n-Heptacosane | 27 | 59.0 |
| n-Hexacosane | 26 | 56.4 |
| n-Pentacosane | 25 | 53.7 |
| n-Tetracosane | 24 | 50.9 |
| n-Tricosane | 23 | 47.6 |
| n-Docosane | 22 | 44.4 |
| n-Hemeicosane | 21 | 40.5 |
| n-Eicosane | 20 | 36.8 |
| n-Nonadecane | 19 | 32.1 |
| n-Octadecane | 18 | 28.2 |
| n-Heptadecane | 17 | 22.0 |
| n-Hexadecane | 16 | 18.2 |
| n-Pentadecane | 15 | 10.0 |
| n-Tetradecane | 14 | 5.9 |
| n-Tridecane | 13 | −5.5 |

Fatty acids of natural oils, alcohols, and waxes may be alternatively be used. Though not intended to be exhaustive, various non-paraffinic PCM's that may be used with the present invention are set forth below.

| Compound | Transition temperature (° C.) |
|---|---|
| Cetyl alcohol | 45–50 |
| Steryl alcohol | 54–57 |
| Lanette wax | 50 |
| Stearic acid (commercial grade) | 52–56 |
| Stearic acid (natural) | 64 |
| Palmitic acid (commercial grade) | 58 |
| Palmitic acid (natural) | 63 |
| Myristic acid | 54 |
| Coconut oil (partially hydrogenated) | 44.5 |
| Sesame oil (partially hydrogenated) | 62.1 |
| Whale oil (partially hydrogenated) | 45.1 |
| Arachis oil (partially hydrogenated) | 51.2 |
| Cottonseed oil (partially hydrogenated) | 38.5 |
| Tallow (fully hydrogenated) | 62 |
| Lard (fully hydrogenated) | 64 |
| Cocoa butter (fully hydrogenated) | 64 |
| Arachis (fully hydrogenated) | 65 |
| Cod liver (fully hydrogenated) | 65 |
| Linseed (fully hydrogenated) | 68 |
| Sesame (fully hydrogenated) | 68.5 |
| Olive (fully hydrogenated) | 70 |
| Poppy (fully hydrogenated) | 70.5 |
| Almond (fully hydrogenated) | 72 |
| Castor wax | 86 |

Phase change materials (PCM's) may be used to enhance thermal therapy by extending the therapeutic life of any thermoactive material. Specifically, a PCM may be used to control the heat generated, emitted, or consumed by a thermal therapy product.

In an instant chemical thermal therapy pack, a salt is separated from water by a membrane. The user is instructed to break the membrane separating the two reagents by twisting, squeezing, or stretching the pack. Usually there is an instant chemical reaction upon mixing of the salt and water that results in a sharp increase or decrease of the local temperature. For instance, in an instant hot pack, heat can be generated by dissolving a salt such as calcium chloride in water. This reaction has an exothermic heat of reaction of 215 cal/g. Similarly, in an instant cold pack, heat can be consumed by dissolving a salt such as ammonium nitrate in water. This reaction has an endothermic heat of reaction of 77 cal/g. The heat released or consumed in typical chemical thermal therapy product is rapidly dissipated through the minimal insulation provided by the material from which it is formed.

The advantages of using a PCM in conjunction with an instant hot or cold pack may be seen by examining a typical commercially available chemical cold pack. As described above, a chemical cold pack consumes heat from its surroundings when activated, usually by rupturing a membrane separating two or more reagents. An appropriate PCM positioned inside the thermal therapy product or within the surrounding area modulates the increase or decrease in temperature. As the pack cools, heat is removed from the liquid PCM, causing it to undergo a phase change, i.e., to solidify or freeze. The solidified PCM maintains the decreased temperature for an extended period of time, as it will require heat to cause the PCM to undergo a phase change back to the liquid state. The heat required to melt the PCM does not contribute to a rise in the temperature until all of the solidified PCM has melted. Thus, the temperature experienced by the user does not increase as rapidly. In this manner it is possible to manage the heat flow to provide a comfortable therapeutic temperature and extend the duration of the therapeutic benefit.

There are other advantages of using a PCM in conjunction with traditional thermal therapy products. First, a greater selection of chemical reagents may be used in a chemical pack without concern for undesirable temperature peaks. As heat is rapidly absorbed or released, the PCM modulates the temperature actually experienced by the user. This provides a significant advantage over traditional thermal therapy products that are limited to certain reaction chemistries that generate or consume a certain amount of heat for some duration at a given solute concentration. Furthermore, for the same quantity of reagents, a longer duration of therapy may be provided, and in some instances, the quantity of reagents may be decreased so a less bulky product may be made.

There are various considerations in selecting an appropriate PCM and the mass of phase change material to be used for a given application. First, the minimum or maximum temperature to be experienced by the user must be determined. For example, for an infant heel warmer application, the maximum permissible temperature may be about 104° F. (40° C.).

For some adult warming applications, such as short-term spot treatment, the maximum experienced temperature may be about 130° F. (54° C.). For some adult applications, such as long-term patient warming, the maximum experienced temperature may be about 108° F. (42° C.). For other adult warming applications, the minimum experienced temperature may be about 99° F. (37° C.).

For some adult cooling applications, such as short-term spot treatment, the minimum experienced temperature may be about 33° F. (0° C.). For other adult cooling applications, the minimum experienced temperature may be about 39° F. (4° C.). For some adult cooling applications, the maximum experienced temperature may be abut 99° F. (37° C.).

Once the desired temperature for a given application is established, at least one PCM having a transition temperature near that temperature is selected so the PCM will undergo a phase transition at or near the desired therapeutic temperature. The amount of PCM used for a given application depends on the amount and type of the thermoactive material used. In general, enough PCM should be used so that all of the heat released or absorbed by the thermoactive material is fully utilized in effecting a phase change of the PCM.

In some embodiments, the present invention may be used to extend the therapeutic benefit of a cold therapy product. In such instances, the PCM may have a transition temperature of from about −10° C. to about 40° C. More particularly, in some embodiments, the PCM may have a transition temperature of from about 0° C. to about 37° C. Examples of PCM's that may be used include, for example, n-tridecane, n-tetradecane, n-pentadecane, n-hexadecane, n-heptadecane, n-octadecane, n-nonadecane, n-eicosane, and combinations thereof. However, it should be understood that other suitable PCM's may be used.

Alternatively, the present invention may be used to extend the therapeutic duration of a heat therapy product. In such instances, the PCM may have a transition temperature of from about 35° C. to about 65° C. More particularly, in some embodiments, the PCM may have a transition temperature of from about 37° C. to about 54° C. Examples of PCM's that may be used include, for example, n-eicosane, n-hemeiconsane, n-docosane, n-tricosane, n-tetracosane, n-pentacosane, n-hexaconsane, n-heptacosane, n-octacosane, and combinations thereof. However, it should be understood that other suitable PCM's may be used.

For some applications, it may be desirable to use multiple PCM's to further extend the therapeutic duration of the thermoactive material. In some embodiments, the combination of PCM's may be chosen so that all of the PCM present undergoes a phase transition at or near the desired therapeutic temperature. In other embodiments, the PCM's may be chosen to provide therapy at two or more temperature levels. Any of the above PCM's may be used as additional PCM's. It should be understood, however, that other PCM's are available and any suitable PCM may be used.

Incorporation of the PCM into the thermal therapy sleeve presents unique challenges. Many PCM's are liquids or become liquids at the transition temperature, and therefore need to be contained in some manner to prevent leakage from the product into which the PCM is incorporated. One means of containing a liquid PCM is to enclose a quantity of the PCM in a discrete pocketed region or hollow chamber within the product. When the PCM becomes a liquid, it is then contained within the space provided and is not able to migrate to other regions or outside of the product.

Alternatively, PCM's that become a liquid at the transition temperature may be encapsulated in the form of microparticles using a temperature-stable material, for example, silica, as the outer shell. The encapsulated PCM is then able to consume or release heat in a reversible manner when exposed to temperatures higher or lower than its melting point. When a PCM is adsorbed onto silica particles, such as those obtained from Phase Change Laboratories, Inc. (10109 Carroll Canyon Road, San Diego, Calif. 92131), the silica particles maintain their dry powder-like properties even at temperatures above the transition temperature.

Encapsulated PCM's may be incorporated into various substrates using a multitude of techniques. Examples of such techniques include applying a coating of an encapsulated PCM on the surface of fibers or films such that the particles adhere to the fiber or film surface, integrating the encapsulated PCM into polymeric fibers, co-extruding fibers from aqueous solutions of polymers mixed with a slurry of an encapsulated PCM, confining the encapsulated PCM in the blister of a blister-pack type laminate, impregnating the encapsulated PCM into a polymeric foam, dispersing the encapsulated PCM in a polymeric resin and subsequently crosslinking the resin to entrap the particles in the polymer matrix, entangling the encapsulated PCM within a fine fiber nonwoven material structure during the manufacturing process, and printing the encapsulated materials onto the substrate.

Any suitable technique or plurality of techniques may be used to incorporate the PCM into the thermal therapy sleeve of the present invention, and the technique selected may depend on the design of the product into which the PCM is incorporated.

The design of the sleeve may vary for a given application. It may be sized or shaped so that a particular part of the body may be exposed or covered entirely. It may include adhesive, ties, or other means to fasten the product to the body or clothing of the user. It may include aesthetic features, such as a cotton or nonwoven outer cover to improve comfort for the user. It may be sealable or may be open on one or more edges for easy insertion and removal of the thermoactive material. It may include one or more insulating materials to improve performance and comfort.

In one embodiment depicted in FIG. 1, the thermal therapy sleeve 50 may include a first layer 52 including an array of non-communicating chambers 54 or pockets containing a first PCM 56. It may further include a second layer 58 joined to the second layer to form at least a partial enclosure having an opening 60 through which a thermoactive material (not shown) may be inserted and removed. In some embodiments, the second layer may include an array of non-communicating chambers containing a second PCM. The first PCM may, in some instances, be chemically identical to the second PCM.

Figure 2:
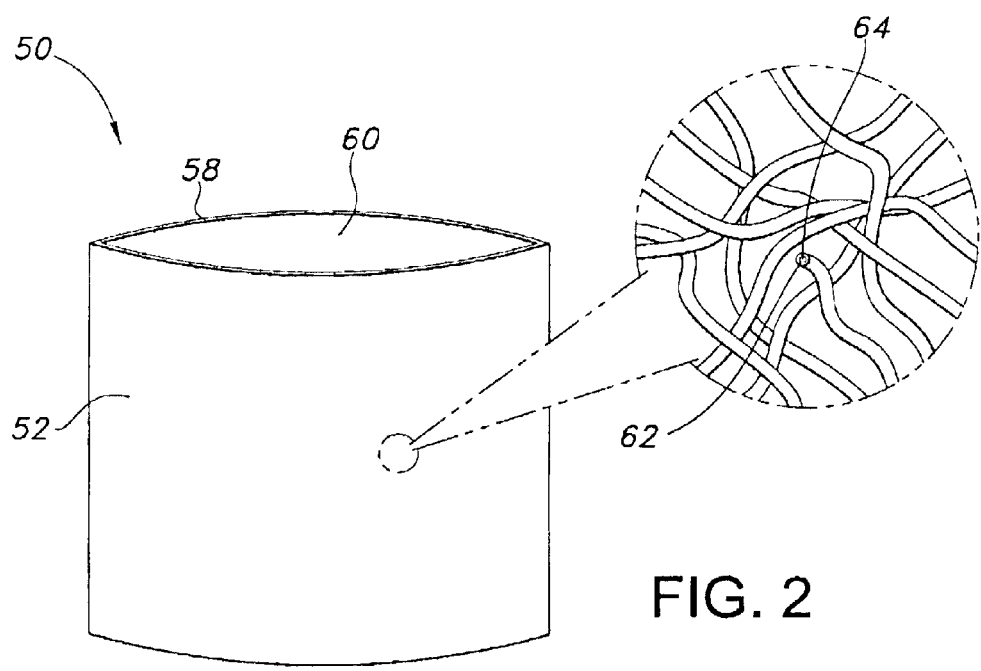
FIG. 2 depicts an exemplary thermal therapy sleeve for use with the present invention, where a layer of the sleeve is formed from a coextruded polymer and phase change material.

In another embodiment depicted in FIG. 2, the PCM may be incorporated directly into fibers that form a layer 52 of the sleeve 50 by coextruding the PCM with a polymeric material. This process may result in a polymeric fiber sheath 62 having a PCM core 64. It may alternately result in a fiber having a side-by-side configuration in which there is a polymer portion and a PCM portion. Other possible configurations will be known to those of skill in the art. Any polymer may be used, and in some embodiments, the polymeric fiber is formed from a polyolefin, such as polypropylene or polyethylene. In some embodiments, the resulting fiber may include from about 1 mass % to about 50 mass % PCM. In other embodiments, the fiber may include from about 5 mass % to about 30 mass % PCM. In yet other embodiments, the fiber may include from about 10 mass % to about 20 mass % PCM.

In such an embodiment, the thermal therapy sleeve 50 may include a first layer 52 formed from a matrix of fibers, where the fibers may include a polymer 62 and at least one PCM 64. The sleeve may include second layer 58 joined to the first layer to form at least a partial enclosure having an opening 60 through which a thermoactive material (not shown) may be inserted and removed. In some embodiments, the second layer may also include a matrix of fibers, where the fibers may be formed from a polymer and at least one PCM. A benefit of using such a composite fiber in a thermal therapy sleeve is that a higher mass of PCM by percent may be obtained. Additionally, the PCM is integral to the structure, so there is little risk that the PCM will mobilize and leak out of the sleeve.

Figure 3:
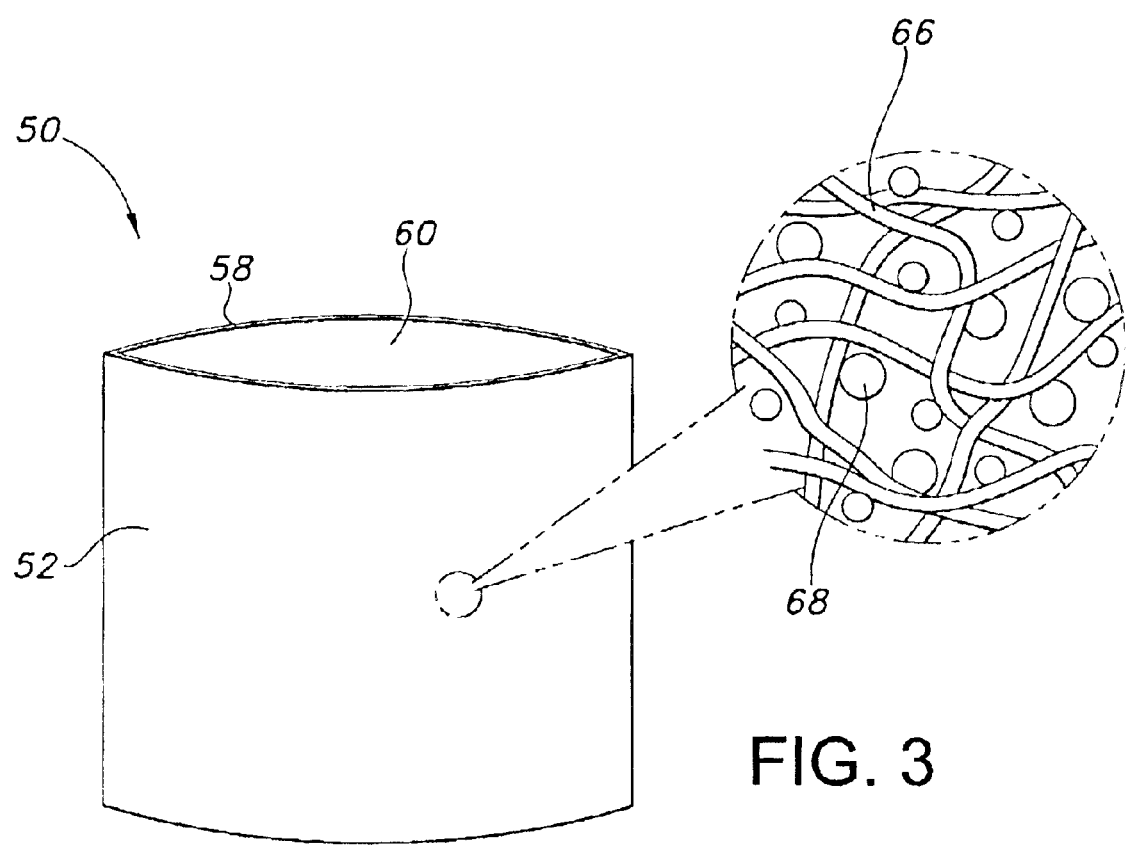
FIG. 3 depicts an exemplary thermal therapy sleeve for use with the present invention, where a layer of the sleeve is formed from a matrix of fibers and an encapsulated phase change material.

In yet another embodiment depicted in FIG. 3, the PCM may be incorporated into the sleeve by physically entangling an encapsulated PCM within the polymeric fiber matrix during or after formation of the fibers. The low mass of the particles enables them to adhere to the fibers by electrostatic forces. Addition of particles to various substrates, particularly nonwoven or airlaid materials is well-known in the art. In some embodiments, the resulting matrix may include from about 1 mass % to about 70 mass % encapsulated PCM. In other embodiments, the matrix may include from about 25 mass % to about 50 mass % encapsulated PCM. In yet other embodiments, the matrix may include from about 30 mass % to about 40 mass % encapsulated PCM.

Where this approach is used, the thermal therapy sleeve 50 may include a first layer 52 formed from a matrix of polymeric fibers 66 and an encapsulated PCM 68, and a second layer 58 joined to the first layer to form at least a partial enclosure having an opening 60 through which a thermoactive material (not shown) may be inserted and removed. In some embodiments, the second layer may also include a matrix of polymeric fibers and a second encapsulated PCM. The second encapsulated PCM may, if desired, be chemically identical to the first encapsulated PCM.

Any suitable method of incorporating a PCM into the present invention may similarly be used to form a sleeve having multiple PCM's, and the PCM's may be incorporated into the same layer or separate layers. Such a sleeve may be used where two therapeutic temperatures are desired. A sleeve that offers such dual functionality may provide a benefit to the user, such as product versatility and user convenience. For instance, the present invention contemplates a sleeve that may be used with both heat and cold therapy. One such sleeve may include a first side or layer that may be placed in contact with the user when a cold therapy product is used as the thermoactive material, and a second side or layer that may be placed in contact with the user when a heat therapy product is used as the thermoactive material. Alternatively, the sleeve may include the PCM's needed to extend both a cold benefit and a heat benefit within the same layer or on the same side of a sleeve so that a user may receive the extended therapeutic benefit of heat or cold therapy on one side of the sleeve, or on both sides of the sleeve simultaneously.

For instance, in one embodiment, the thermal therapy sleeve may include a first layer into which a first PCM has been incorporated, and a second layer into which a second PCM has been incorporated. As stated previously, the PCM's may be chemically identical, similar, or distinct, depending on the application and the desired therapeutic temperature and duration. In one embodiment, the first PCM may have a transition temperature of from about −10° C. to about 40° C., and the second PCM may have a transition temperature of from about 35° C. to about 65° C. In another embodiment, the first PCM may have a transition temperature of from about 0° C. to about 37° C., and the second PCM may have a transition temperature of from about 37° C. to about 54° C.

In another embodiment, the sleeve may include a first layer into which a first PCM and a second PCM are incorporated. In one such embodiment, the first PCM may have a transition temperature of from about −10° C. to about 40° C. and the second PCM may have a transition temperature of from about 35° C. to about 65° C. In another such embodiment, the first PCM may have a transition temperature of from about 0° C. to about 37° C. and the second PCM may have a transition temperature of from about 37° C. to about 54° C. In some embodiments, such a sleeve may include a second layer into which a third PCM is incorporated. The third PCM may be chemically identical, similar, or distinct from the first and second PCM's. While a sleeve with three PCM's is described herein, it should be understood that additional PCM's may be used depending on the application and the desired therapeutic temperature and duration.

The layers of the sleeve may be made from a wide variety of materials, including, for example, woven reusable fabrics and nonwoven disposable fabrics or webs. Nonwoven materials suitable for use with the present invention include, for example, a multilayer laminate such as a spunbond/meltblown/spunbond ("SMS") material. An example of such a fabric is disclosed in U.S. Pat. No. 4,041,203 and is hereby incorporated by reference.

As used herein the term "nonwoven fabric or web" means a web having a structure of individual fibers or threads that are interlaid, but not in an identifiable manner as in a knitted fabric. Nonwoven fabrics or webs have been formed from many processes such as for example, meltblowing processes, spunbonding processes, and bonded carded web processes.

As used herein the term "spunbond fibers" or "spunbonded fibers" refers to small diameter fibers which are formed by extruding molten thermoplastic material as filaments from a plurality of fine, usually circular capillaries of a spinneret with the diameter of the extruded filaments then being rapidly reduced, for example, as in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns.

As used herein the term "meltblown fibers" means fibers formed by extruding a molten thermoplastic material through a plurality of fine, usually circular, die capillaries as molten threads or filaments into converging high velocity, usually hot, gas (e.g. air) streams that attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers that may be continuous or discontinuous, are generally smaller than 10 microns in average diameter, and are generally tacky when deposited onto a collecting surface.

As used herein the term "multilayer laminate" means a laminate in which some of the layers are spunbond or some meltblown such as a spunbond/meltblown/spunbond (SMS) laminate and others as disclosed in U.S. Pat. No. 4,041,203 to Brock et al., U.S. Pat. No. 5,169,706 to Collier, et al., U.S. Pat. No. 5,145,727 to Potts et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (6 to 400 gsm), or more particularly from about 0.75 to about 3 osy. Multilayer laminates may also have various numbers of meltblown layers or multiple spunbond layers in many different configurations and may include other materials like films or conform materials, e.g. SMMS, SM, SFS, etc.

As used herein the term "conform" means a process in which at least one meltblown diehead is arranged near a chute through which other materials are added to the web while it is forming. Such other materials may be pulp, superabsorbent particles, cellulose or staple fibers, for example. Conform processes are shown in commonly assigned U.S. Pat. No. 4,818,464 to Lau and U.S. Pat. No. 4,100,324 to Anderson et al. Webs produced by the conform process are generally referred to as "conform materials".

The sleeve may also include a metallized film, foil, or the like. One material that may be suitable for use with the present invention is a metallized plastic film, for example, SilverPAK® polyester barrier, available from Kapak Corporation of Minneapolis, Minn.

The components of the sleeve may be produced separately and assembled by for example, thermal bonding, adhesive bonding, ultrasonic bonding, or stitching. Other means of assembly will be readily known by those of skill in the art. Alternatively, each layer of the sleeve may be constructed as a single multilayer unit followed by die cutting and some means to join the layers. The layers of the sleeve may be joined at any suitable location as desired. Thus, the layers may be joined at or near a single edge, or at or near a plurality of edges, as desired or needed to accomplish the purpose of the present invention.

The components of the sleeve may be chemically, mechanically, electrostatically, or otherwise treated to provide additional functional or aesthetic attributes, such as softness, stretch, absorbency, repellency, odor reduction, skin care, or the like.

The present invention further contemplates a thermal therapy system having an extended therapeutic duration. The system includes a thermoactive material that may include a chemical pack sized to fit within a thermal therapy sleeve. The pack may be divided into at least a first compartment and a second compartment by a membrane, where the first compartment contains a solute and the second compartment contains a solvent, and where the rupturing of the membrane causes the combination of the solute and solvent and produces an endothermic reaction or an exothermic reaction. The system may further include a flexible sleeve including a first layer into which a first PCM is incorporated, and a second layer joined to the first layer to form at least a partial enclosure having an opening through which the thermoactive material may be inserted and removed. In some embodiments, the second layer may include a second PCM, that may, if desired, be chemically identical to the first PCM.

The PCM may be incorporated into the sleeve using any suitable technique. In some embodiments, the first layer may include an array of non-communicating chambers containing the first PCM. In other embodiments, the first layer may include a matrix of fibers, where the fibers are formed from a polymer and the first PCM. In yet other embodiments, the first layer may include a matrix of polymeric fibers and the first PCM. In such embodiments, the PCM may be encapsulated. In all such embodiments described above, additional layers having additional PCM's may be incorporated, and any suitable technique may be used to incorporate the second PCM into the second layer.

In yet other embodiments, a PCM may be included within the thermal therapy product in addition to including the same or another PCM within the sleeve. In one embodiment, the thermal therapy product may be a chemical pack including one or more PCM's. The PCM may be incorporated into the pack as a separate component separated by a membrane or may be mixed with the solute or solvent, or both, as desired. In another embodiment, the thermal therapy product may be a gel-based product that includes one or more PCM's. In yet another embodiment, the thermal therapy product may be a metal oxidation product that includes one or more PCM's.

The present invention further contemplates a method of extending the therapeutic life of a thermal therapy product. The method generally includes selecting a thermal therapy product to provide a benefit to a user, selecting a PCM, incorporating the PCM into a thermal therapy sleeve and placing the thermal therapy product inside the thermal therapy sleeve. The sleeve may be any sleeve contemplated by the present invention and may include first layer and a second layer, where the first layer is joined to the second layer to form at least a partial enclosure having an opening through which the thermal therapy product may be inserted and removed. The thermal therapy product may be selected to provide a heat benefit to the user. Alternatively, the thermal therapy product may be selected to provide a cold benefit to the user. Any suitable PCM or combination of PCM's may be used as described herein.

The method may also include activating the thermal therapy product. The technique by which the product is activated depends on the type of product selected by the user. In one embodiment, the thermal therapy product may include a chemical pack that is activated by breaking a membrane that separates two reagents. For example, a chemical heat pack may include a first compartment and a second compartment separated by a membrane, where the first compartment contains a solute and the second compartment contains a solvent. The rupturing of the membrane in a heat pack causes the combination of the solute and solvent and produces an exothermic reaction. Likewise, a chemical cold pack may include a first compartment and a second compartment separated by a membrane, where the first compartment contains a solute and the second compartment contains a solvent. The rupturing of the membrane in a cold pack causes the combination of the solute and solvent and produces an endothermic reaction. Such chemical packs are generally disposable. For some warming applications, the exothermic reaction of calcium chloride and water may be used. For some cooling applications, the endothermic reaction of ammonium nitrate and water may be used. However, it should be understood that other exothermic and endothermic reaction chemistries are contemplated by the present invention. Such products may be activated before insertion into the sleeve, or after insertion, as desired.

In another embodiment, the product is a gel-based product that is activated by exposing it to an energy source. One such product may be activated by placing it in a cool environment, such as a refrigerator, to provide cold therapy. In yet another embodiment, the product is a gel-based product that is activated by placing it in a warm environment, such as a microwave oven, to provide heat therapy. Such gel-based products may be reusable upon regeneration, i.e., repeated exposure to the appropriate energy source or temperature environment.

In still another embodiment, the thermal therapy product is a metal oxidation product, for example, an iron oxidation product, that is activated by exposing the product to air. Such products are often disposable.

The method of the present invention further includes removing the thermal therapy product from the sleeve for disposal, regeneration, or replacement of the product. In this manner, the sleeve may be used multiple times for heat or cold therapy or may be regenerated to continue the therapeutic benefit of a particular heat or cold therapy session.

The present invention further contemplates a method of making a thermal therapy system having an extended therapeutic life. The method includes selecting a solute and a solvent such that the mixing of the solute and the solvent results in an endothermic or exothermic reaction, and depositing the solute and the solvent in a pack. The pack may be divided into at least a first compartment and a second compartment by a membrane, where the first compartment contains the solute and the second compartment contains the solvent. The rupturing of the membrane causes the mixing of the solute and solvent. Any suitable chemical reagents may be used as described above.

The method further includes selecting a PCM and incorporating the PCM into a thermal therapy sleeve. The sleeve may be any sleeve contemplated by the present invention, and may include a first layer and a second layer, where the first layer is joined to the second layer to form at least a partial enclosure having an opening through which the pack may be inserted and removed. The method further includes placing the pack into the thermal therapy sleeve, and activating the pack.

The present invention also contemplates a method of making a thermal therapy system having an extended therapeutic life. The method includes providing a reusable heat or cold thermal therapy product, selecting a PCM, incorporating the PCM into a thermal therapy sleeve, and providing an energy source to activate the product prior to placing the product into a thermal therapy sleeve. The sleeve may be any thermal therapy sleeve contemplated by the present invention, and may include a first layer and a second layer, where the first layer is joined to the second layer to form at least a partial enclosure having an opening through which the product may be inserted and removed.

So that the invention may be more readily understood, reference is made to the following examples. The examples are intended to be illustrative of the invention but are not intended to be limiting in scope.

EXAMPLE 1

The ability to modulate the temperature of a chemical heat product using a PCM was demonstrated. In this example, the sleeve was constructed from a nonwoven material, as described below.

Preparation of Control Sleeve

Two pieces of a 2.0 ounces per square yard (osy) fine fiber polypropylene meltblown nonwoven material were laminated together to prepare the first layer of the control sleeve. A 12 in. (304 mm) by 12 in. (304 mm) Carver hot press (Carver model 1523) was used to laminate the materials together at a temperature of 145° C. and a pressure of 12,000 psi for 2 minutes. Another two pieces of the same material were laminated together in the same manner to prepare the second layer of the control sleeve. An ultrasonic bonder was then used to bond the two laminates on three sides to form the control sleeve. The resulting sleeve had a mass of about 7.0 g.

Preparation of Experimental Sleeve

Two pieces of a 2.0 ounces per square yard (osy) fine fiber polypropylene meltblown nonwoven material were laminated together to prepare the first layer of the experimental sleeve. A 12 in. (304 mm) by 12 in. (304 mm) Carver hot press (Carver model 1523) was used to laminate the materials together at a temperature of 145° C. and a pressure of 10,000 psi for 2 minutes. Prior to lamination, about 7.2 g of 127° F. (53° C.) transition temperature PCM (available from Phase Change Laboratories, Inc. of San Diego, Calif.) was placed between the layers. The resulting mass of the first layer was about 10.7 g.

Another two pieces of the same material were laminated together in the same manner to prepare the second layer of the experimental sleeve. Prior to lamination, about 6.9 g of 127° F. (53° C.) transition temperature PCM (available from Phase Change Laboratories, Inc. of San Diego, Calif.) was placed between the layers. The resulting mass of the second layer was about 10.1 g.

An ultrasonic bonder was then used to bond the two laminates on three sides to form the experimental sleeve. The resulting sleeve contained about 67.8 mass % of PCM.

Preparation of Chemical Pack

A metallized plastic film laminate (SilverPAK® 2.5 mils (0.025 in.) thick polyester barrier from Kapak Corporation of Minneapolis, Minn.) was used to make a pouch to hold approximately 10 g of calcium chloride ($CaCl_2$) powder (VWR Catalog number EM-CX0156-1). A 4.5 in. (114 mm) by 4.5 in. (114 mm) pouch was made by bonding the laminates on three sides using an ultrasonic bonder. After filling the pouch with the $CaCl_2$ powder, the fourth side of the pouch was sealed using a pressure sensitive adhesive tape.

Experimental Design

Figure 4:
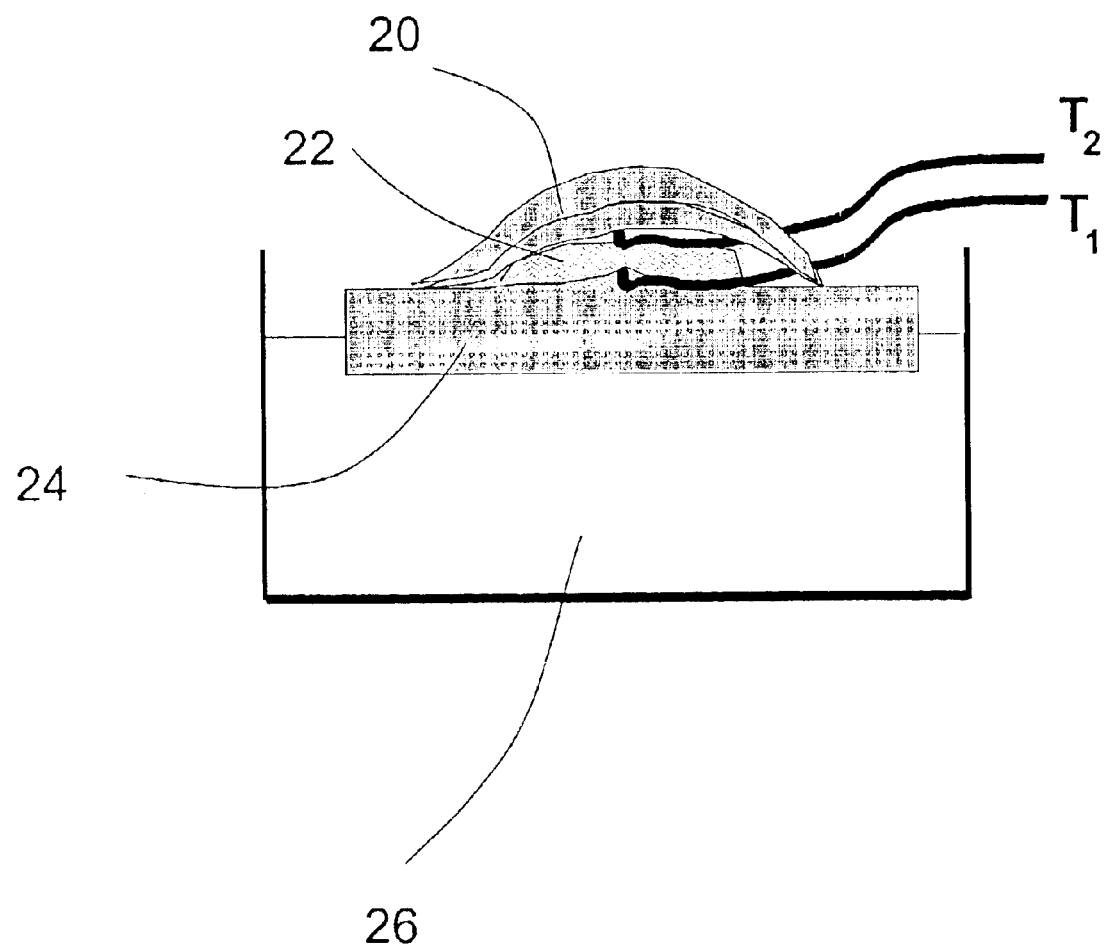
FIG. 4 depicts the experimental setup used to measure time-temperature data for various thermal therapy systems evaluated in Examples 1 and 2.

The experimental setup depicted in FIG. 4 was used to measure the temperature profile of the $CaCl_2$ hot pack upon introduction of 10 ml of deionized water. Polystyrene foam insulation 20 was used to cover the sample 22. The control and test sleeves were enclosed in another SilverPAK® layer to obtain a uniform surface temperature. The sample 22 was placed on an aluminum plate 24 in contact with the surface of a circulating water bath 26 to provide a constant temperature. Two temperature measurements were taken: $T_1$, the temperature between the bottom surface of the sample and the metal plate, and $T_2$, the temperature between the top surface of the sample and the insulation.

Results

Figure 5:
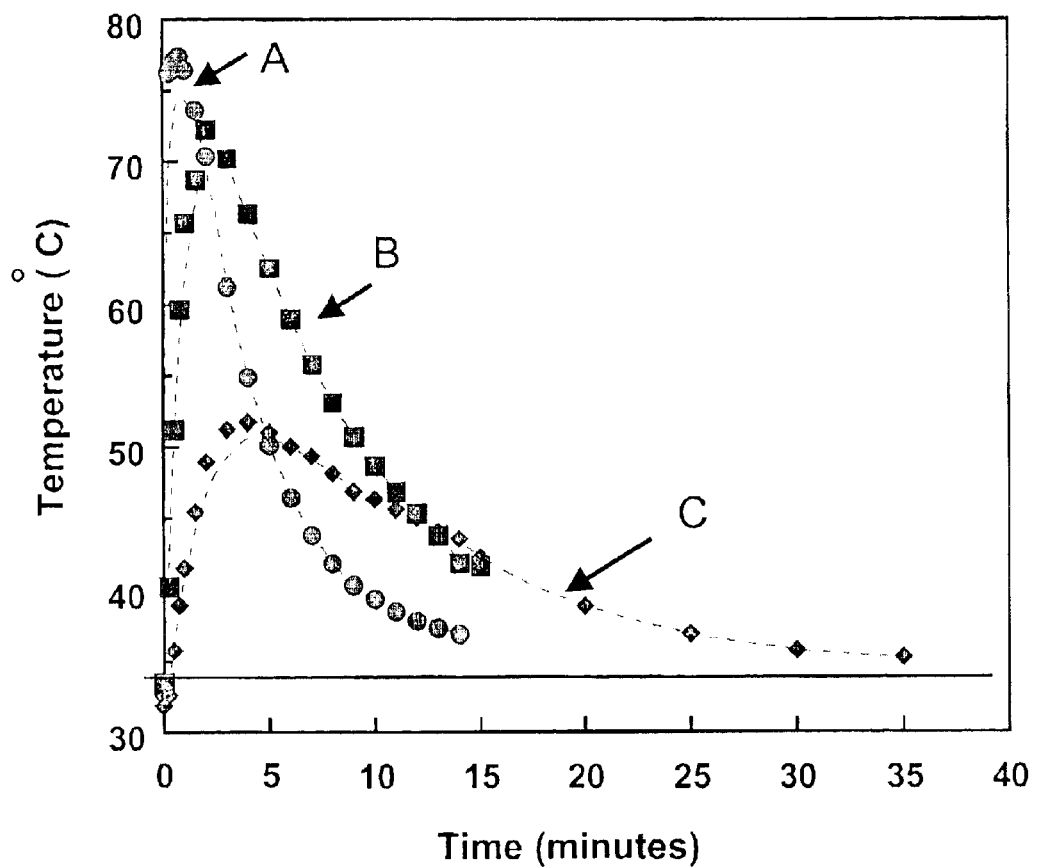
FIG. 5 depicts a comparison of time-temperature profiles for three exemplary calcium chloride chemical pack systems evaluated.

FIG. 5 depicts the temperature profile for $T_2$ as a function of time for the three cases evaluated: the foil pouch containing calcium chloride (depicted as curve A); the foil pouch with calcium chloride inserted into the control sleeve (depicted as curve B); and $T_2$ for the foil pouch with calcium chloride inserted into the test sleeve (depicted as curve C). Curve C shows a reduced peak temperature and an extended duration. Thus, the results indicate that the presence of PCM in the test sleeve modulates both the peak temperature and the duration of heat release from the calcium chloride pack.

EXAMPLE 2

The ability to modulate the temperate of a chemical pack using a PCM was demonstrated. In this example, the sleeve was constructed from a metallized film as described below.

Preparation of Control Sleeve D

Two pieces of a metallized plastic film laminate bag (SilverPAK® 2.5 mils (0.025 in. thickness) polyester barrier from Kapak Corporation of Minneapolis, Minn.) were sealed together using epoxy adhesive. Note that this sleeve did not have a pocketed laminate structure of control sleeve E and experimental sleeve F.

Preparation of Control Sleeve E

Two pieces of the same metallized plastic film laminate bag were laminated together to prepare the first layer of the control sleeve. The pieces were laminated using a 12 in. (304 mm) by 12 in. (304 mm) Carver hot press (Carver model 1523) at a temperature of about 135° C. and a pressure of about 10,000 psi for a duration of about 1 minute. Another two pieces of the same material were laminated together in the same manner to prepare the second layer of the control sleeve. A high strength epoxy adhesive was then used to bond two layers on three sides to make the control sleeve. The resulting mass of the sleeve was about 9.0 g.

Preparation of Experimental Sleeve F

Two pieces of a metallized plastic film laminate bag (SilverPAK® 2.5 mils (0.025 in. thickness) polyester barrier from Kapak Corporation of Minneapolis, Minn.) were laminated together to prepare the first layer of the experimental sleeve. Prior to lamination, about 10.7 g of 127° F. (53° C.) transition temperature PCM (available from Phase Change Laboratories, Inc. of San Diego, Calif.) was placed between the two pieces. The pieces were laminated using a 12 in. (304 mm) by 12 in. (304 mm) Carver hot press (Carver model 1523) at a temperature of about 135° C. and a pressure of about 10,000 psi for a duration of about 1 minute. The resulting mass of the first layer was about 15.3 g.

Another two pieces of the same material were laminated together in the same manner to prepare the second layer of the experimental sleeve. Prior to lamination, about 9.8 g of 127° F. (53° C.) transition temperature PCM (available from Phase Change Laboratories, Inc. of San Diego, Calif.) was placed between the layers. The resulting mass of the second layer was about 14.5 g.

A high strength epoxy adhesive was then used to bond two layers on three sides to make the experimental sleeve.

Preparation of Samples D, E, and F

Sample D was then formed by placing 10 g of $CaCl_2$ into control sleeve D and closing the sleeve using an adhesive tape at the open end. Sample E was formed by placing 10 g of $CaCl_2$ into control sleeve E and closing the sleeve using an adhesive tape at the open end. Sample F was formed by placing 10 g of $CaCl_2$ into experimental sleeve F and closing the sleeve using an adhesive tape at the open end. Sample F contained about 68.8 mass % of PCM.

Experimental Design

The samples were then evaluated using the experimental setup used in Example 1. Polystyrene foam insulation was placed on top of each sample to insulate it from the air. A syringe was used to inject 10 ml of deionized water into each sample. The resulting temperature profiles for $T_1$ and $T_2$ were measured as a function of time.

Results

Figure 6:
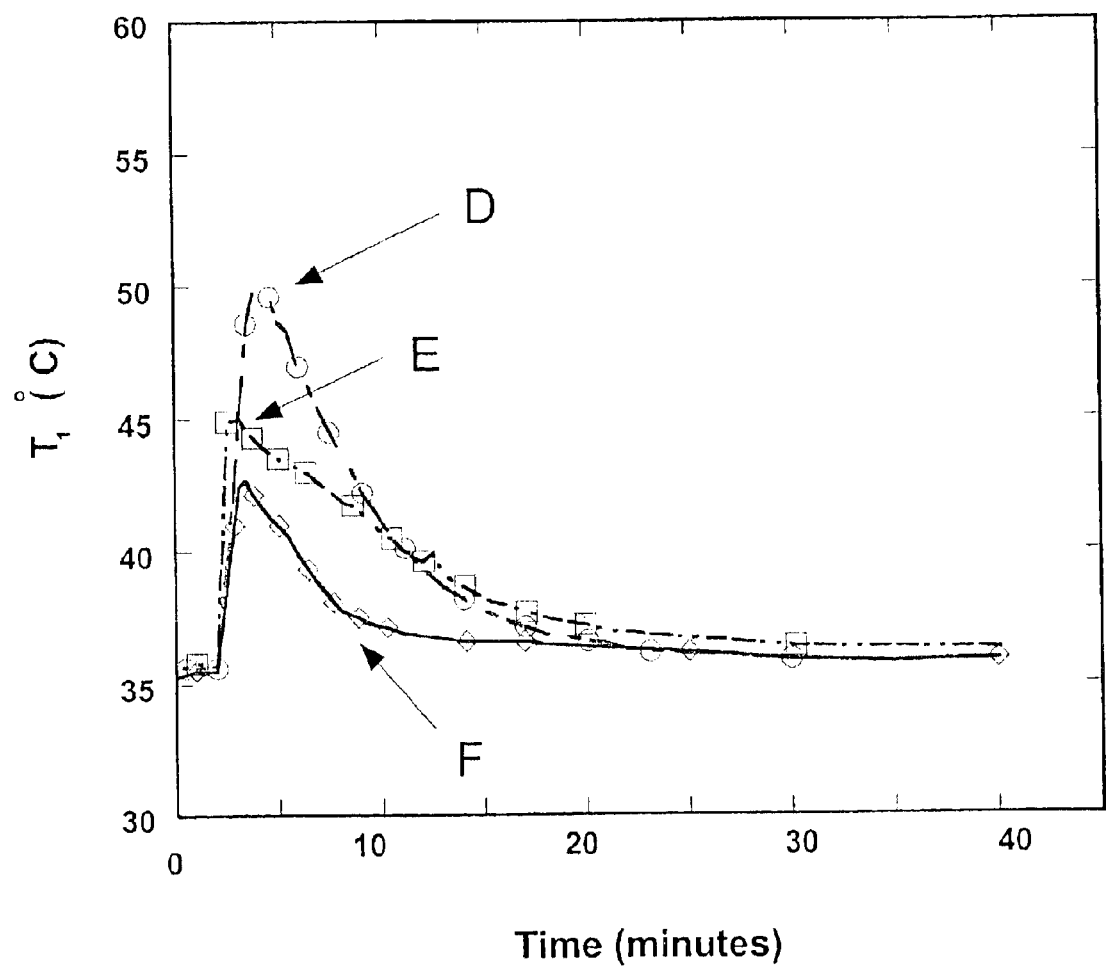
FIG. 6 depicts the temperature between the bottom surface of the sample and the metal plate as a function of time for three exemplary calcium chloride chemical pack systems.
Figure 7:
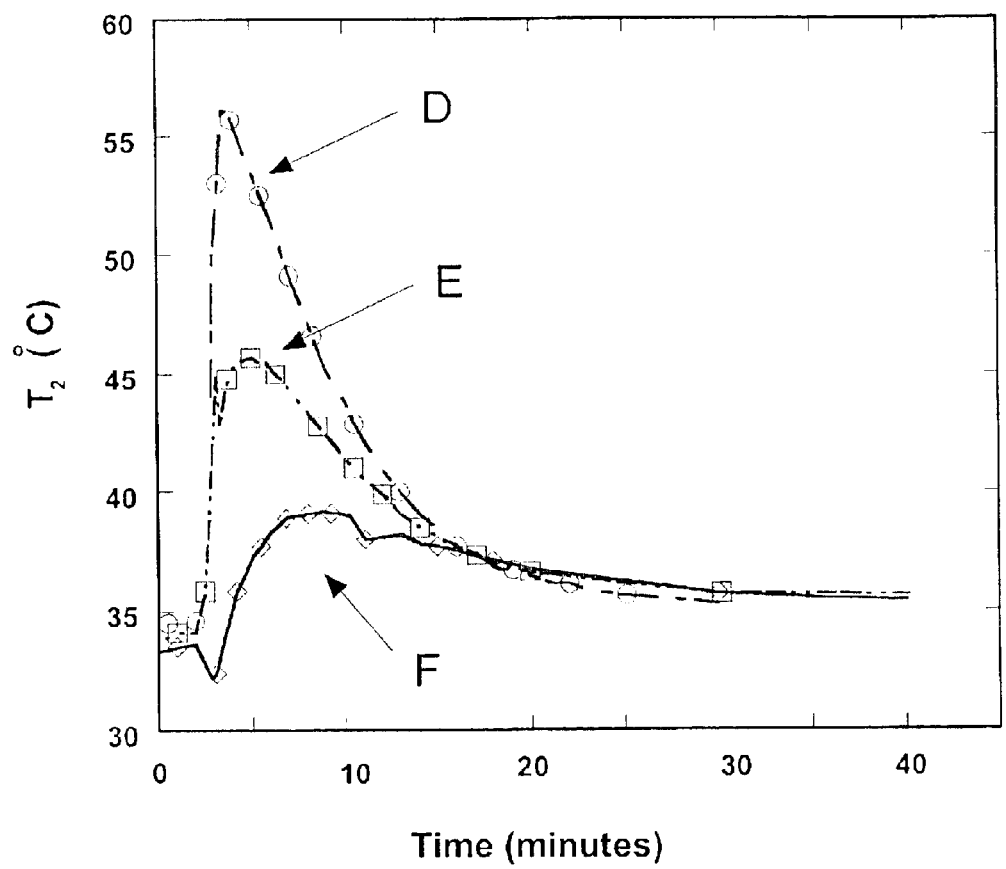
FIG. 7 depicts the temperature between the top surface of the sample and the insulation as a function of time for three exemplary calcium chloride chemical pack systems.
Figure 8:
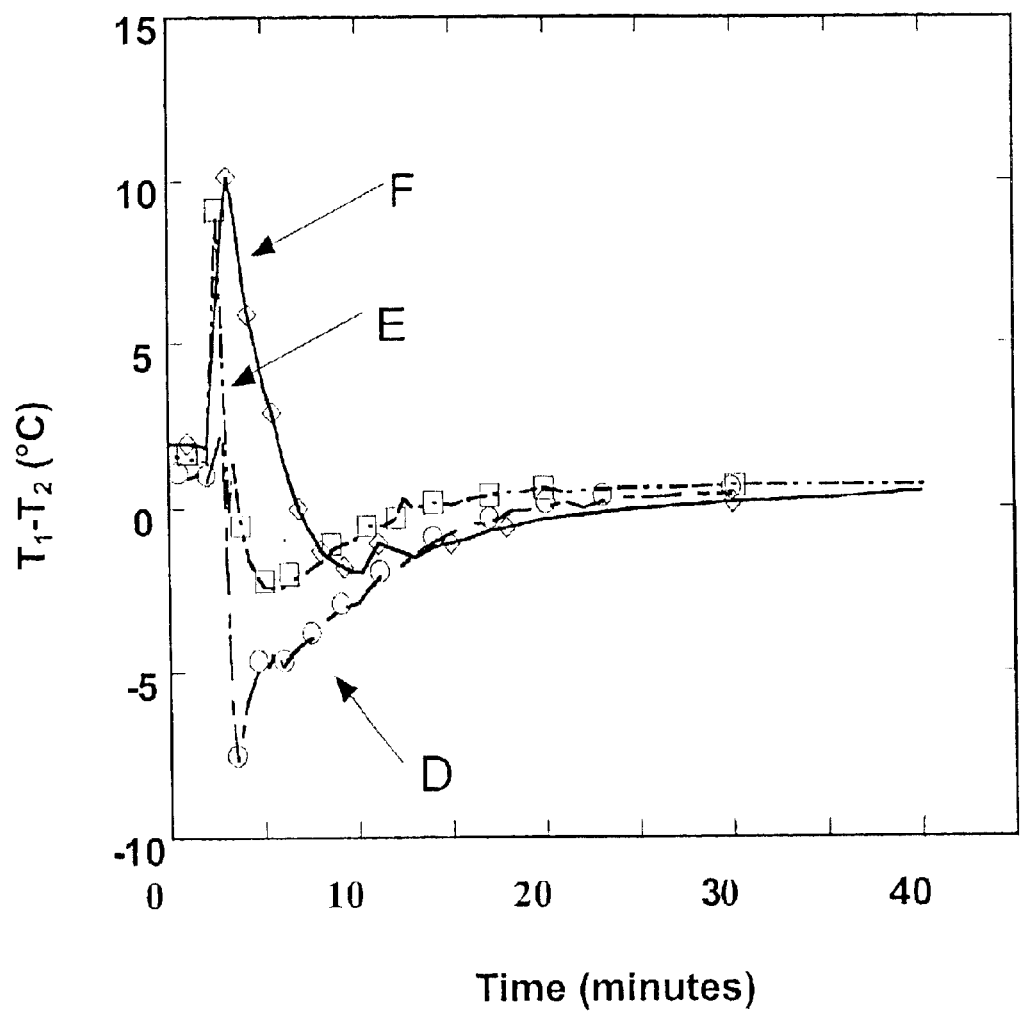
FIG. 8 depicts the difference between the temperature between the bottom surface of the sample and the metal plate and the temperature between the top surface of the sample and the insulation as a function of time for three exemplary calcium chloride chemical pack systems.

FIGS. 6, 7, and 8 show the profiles of $T_1$, $T_2$, and $(T_1-T_2)$, respectively, as a function of time. As seen in FIG. 6, the peak temperature decreased for the experimental sample F containing the PCM as compared with control samples D and E. The experimental sample F exhibited a slightly delayed decay of the temperature with time; however, most of the heat generated was quickly removed through the lower side of the pack to the circulating water bath.

FIG. 7 shows a large plateau in $T_2$ for the experimental sample F compared with the two control samples D and E. Since the heat transfer on the upper side of the sleeve was limited due to the polystyrene foam insulation, there was significant accumulation of heat over time on this surface. In the case of control samples D and E, the decay of accumulated heat was much more rapid than that for the experimental sample F, which contained the PCM.

A much more pronounced difference between the three temperature profiles is seen in FIG. 8. The difference between $T_1$ and $T_2$ was initially positive ($T_1$ is greater than $T_2$), followed by a sharp transition to a negative value ($T_1$ is lower than $T_2$). This indicates that there was a significant heat accumulation on the $T_2$ side once the chemical reaction was initiated. This accumulation of heat was gradually dissipated by heat transfer through the thickness of the sample to the circulating water bath. This decay was much slower for the experimental sample F than for the control samples D and E. The additional heat storage capacity of the PCM in the experimental sample F caused a much slower dissipation of heat.

EXAMPLE 3

The ability to extend the therapeutic duration of a thermal therapy heat pack and modulate the experienced temperature using multiple PCM's was demonstrated.

To understand the effect of combining multiple PCM's within the thermal therapy sleeve, the PCM's were evaluated individually and in combination. The first PCM selected was octacosane (transition temperature of about 61° C., available from Aldrich Chemical under the catalog number O-50-4). The second PCM selected was eicosane (transition temperature of about 37° C., available from Aldrich Chemical under the catalog number 21,927-4).

Small pouches (about 4 in. (102 mm) by about 2 in. (51 mm) were made using two pieces of a metallized plastic film laminate bag (SilverPAK® 2.5 mils (0.025 in. thickness) polyester bar tier from Kapak Corporation of Minneapolis, Minn.). Each was filled with about 10 g of PCM in the liquid state. The first pouch contained octacosane (pouch H), and the second pouch contained eicosane (pouch I). The pouches were sealed using a thermal impulse sealer and allowed to cool to solidify the PCM. A third pouch was made with a 50/50 mixture of octacosane and eicosane (pouch J).

Four chemical heat packs were formed as in Example 2 using the Kapak material. Each pack was filled with about 75 g deionized water. Immediately before taking measurements, about 50 g of $CaCl_2$ was added to the pack. One pack was formed as a control (sample G).

Figure 9:
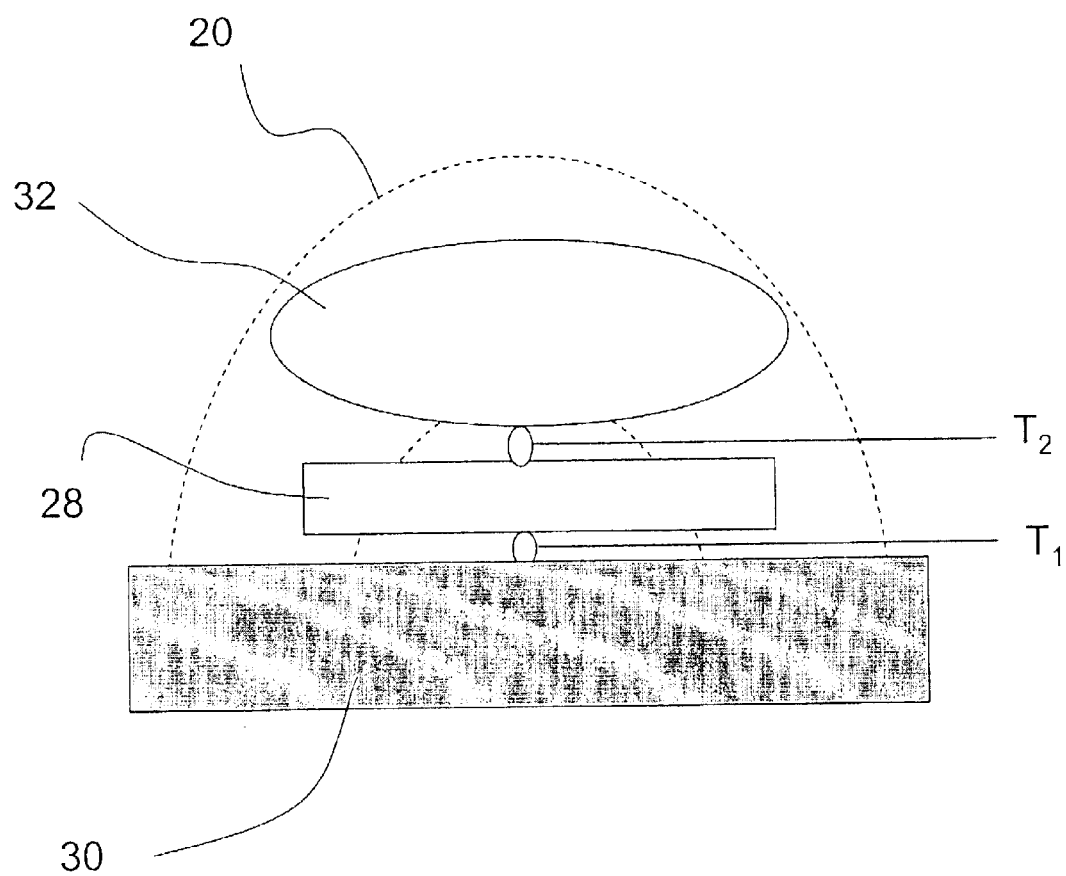
FIG. 9 depicts the experimental setup used to measure time-temperature data for various thermal therapy systems evaluated in Examples 3, 4, and 5.

The experimental setup used in FIG. 9 was used to collect time-temperature data for each of the samples. The sample pouch 28 was placed on the test surface 30. The chemical heat pack 32 was placed on top of the sample pouch 28. Polystyrene foam insulation 20 was used to cover the system. Two temperature measurements were taken: $T_1$, the temperature between the bottom surface of the sample pouch and the test surface, and $T_2$, the temperature between the top surface of the sample pouch and the bottom surface of the chemical pack. The data was collected using a DT9805 A/D board Data Translation) and LabTech Data Acquisition software. The results of the analyses are depicted in FIGS. 10, 11, 12, and 13.

Figure 10:
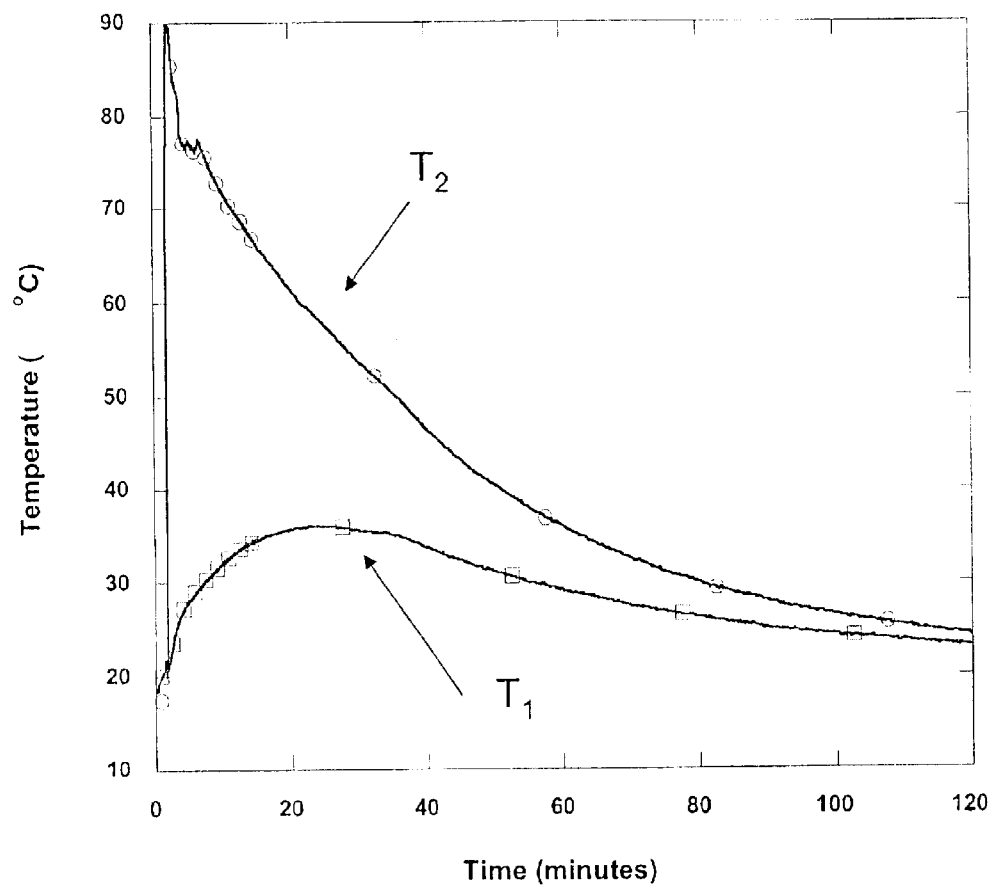
FIG. 10 depicts the temperature as a function of time for an exemplary system including octacosane.

FIG. 10 depicts the results for sample H containing the octacosane. The presence of octacosane lowered the peak temperature that would be felt on the therapeutic side (the side with the PCM that would contact the skin). However, the quantity of heat generated by activation of the hot pack was not enough to melt the entire mass of the phase change material. Therefore, there the heat modulation was not optimized.

Figure 11:
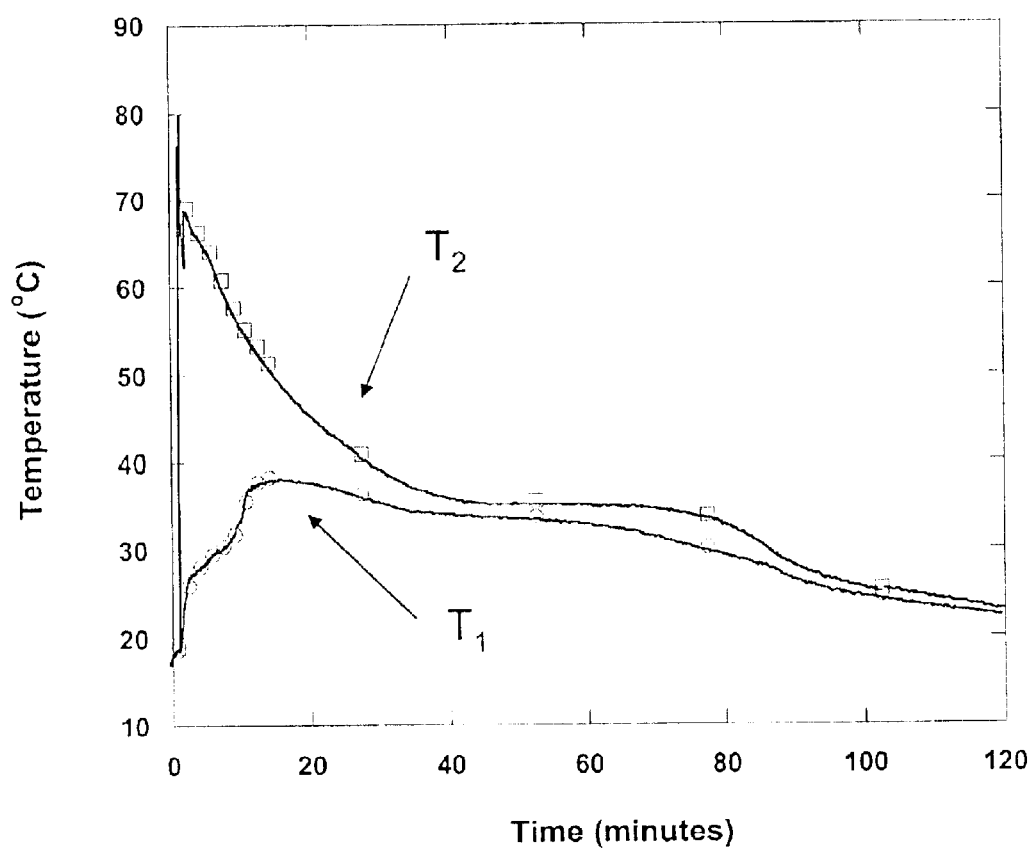
FIG. 11 depicts the temperature as a function of time for an exemplary system including eicosane.

FIG. 11 depicts the results for sample I containing the eicosane. The presence of eicosane lowered the peak temperature and modulated the heat flow since the quantity of heat generated was enough to melt the entire mass of the PCM.

Figure 12:
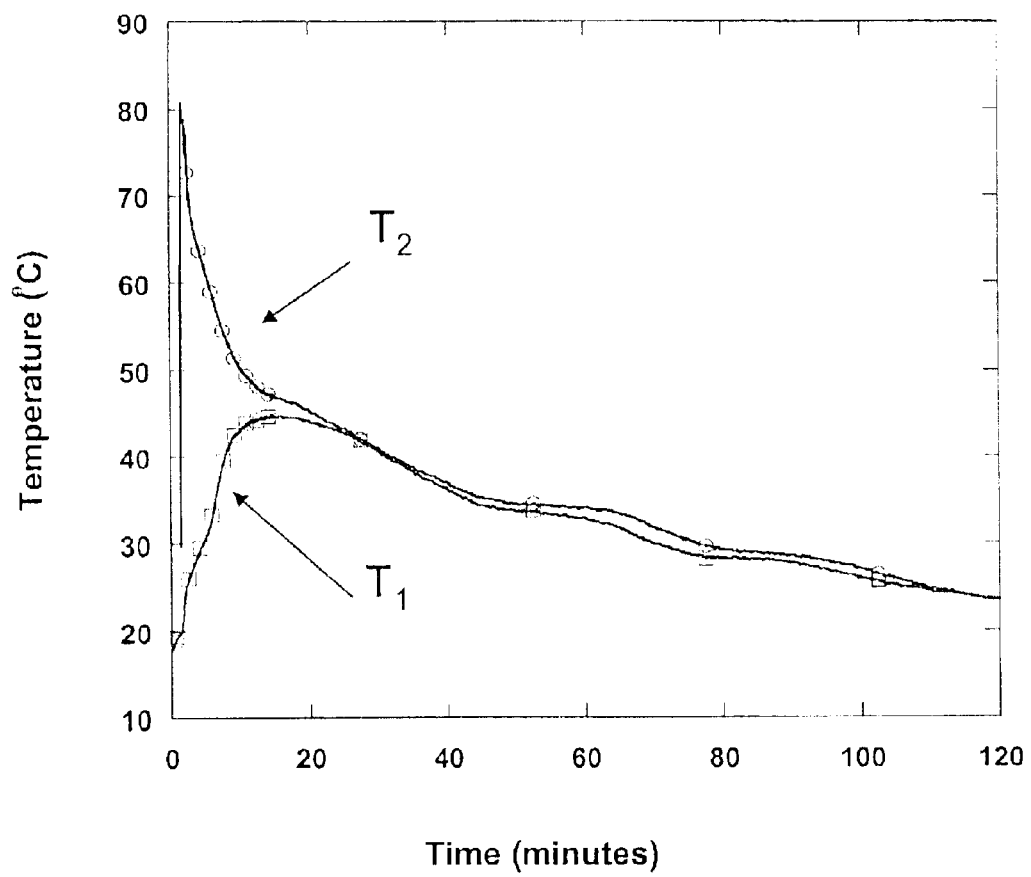
FIG. 12 depicts the temperature as a function of time for an exemplary system including 50/50 mixture of octacosane and eicosane.

FIG. 12 depicts the results for sample J containing the 50/50 mixture of octacosane and eicosane. When mixed in this manner, both octacosane and eicosane influenced the time-temperature profile of the chemical pack. A higher peak temperature was observed due to the presence of the higher melting octacosane. However, only the eicosane melted completely to modulate the heat flow at its transition temperature of 35° C. A summary of the results is presented below.

| PCM | Peak Temperature (Test surface) | $t_{30}$ (time to reach 30° C. during the cooling phase) |
|---|---|---|
| Control (No PCM) | 80–85° C. | 55 minutes |
| Octacosane | 35° C. | 50–60 minutes |
| Eicosane | 38° C. | 80 minutes |
| 50/50 Eicosane/octacosane | 45° C. | 70 minutes |

Figure 13:
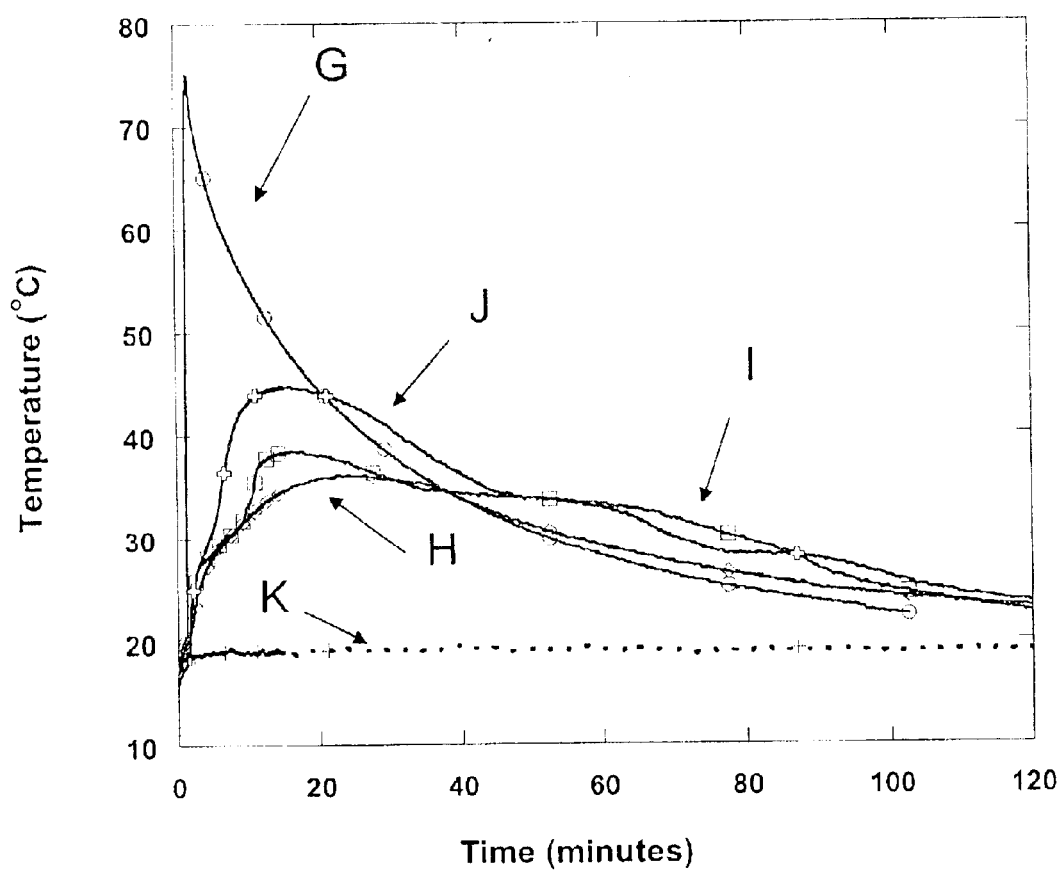
FIG. 13 depicts a comparison of the data of FIGS. 10-12.

As can be seen in FIG. 13, using eicosane in combination with octacosane (curve J), the temperature was modulated at 35° C. and the duration of thermal delivery was increased by approximately 45%, when compared with the control sample (curve G), the octacosane sample (curve H), and the eicosane sample (curve I). Curve K represents an ambient temperature baseline for reference purposes. The results indicate that the peak temperature experienced by the test surface may be raised by using a combination of PCM's. Although there was a slight reduction in total duration of heat delivery, two levels of temperatures may be useful in certain therapies.

EXAMPLE 4

The ability to extend the therapeutic duration of a thermal therapy cold pack and modulate the experienced temperature using multiple PCM's was demonstrated.

The same procedure was carried out as in Example 3, except that a cold pack was used. The following PCM's were used: pentadecane (transition temperature of about 10° C., Aldrich Catalog number P-340-6), tetradecane (sample M, transition temperature of about 6° C., Aldrich Catalog number 17,245-6), and hexadecane (sample N, transition temperature of about 18° C., Aldrich Catalog number 29,631-7). Sample O contained a 50/50 mixture of pentadecane and tetradecane. The chemical pack contained 85 g deionized water, to which 100 g ammonium nitrate ($NH_4NO_3$) was added immediately prior to taking measurements.

Figure 14:
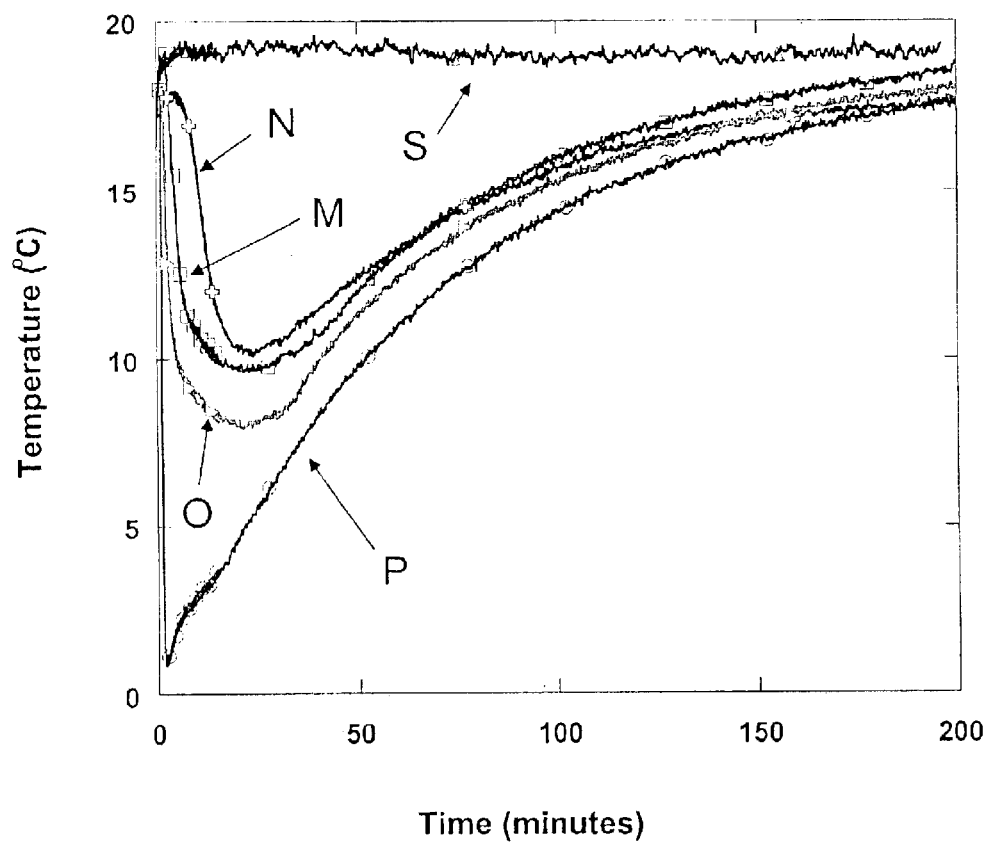
FIG. 14 depicts a comparison of the time-temperature data for various exemplary systems including no phase change material, tetradecane, hexadecane, and a 50/50 mixture of pentadecane and tetradecane.

FIG. 14 depicts a summary of the results. The ambient temperature baseline is presented as curve S. Using the combination of PCM's (curve O), there was a considerable modulation of the peak temperature compared to the control (curve P). The increase in the therapeutic duration was not as readily apparent, since the temperature profile during the re-warming phase was quite shallow. This effect was most likely observed due to the slow, continuous dissolution of the salt in water. Since salt solubility decreases at low temperatures, not all of the salt dissolved in the water immediately. Once the chemical pack began to re-warm, more of the salt dissolved, causing a delay in re-warming. Consequently, the phase change effect was not as prominent as in the case of the instant hot pack. However, there may be applications in which such effects can be minimized.

EXAMPLE 5

The ability to extend the therapeutic duration of both a hot chemical pack and a cold chemical pack using a thermal therapy sleeve with multiple PCM's was demonstrated.

Four small pouches (about 4 in. (102 mm) by about 2 in. (51 mm) were made using two pieces of a metallized plastic film laminate bag (SilverPAK® 2.5 mils (0.025 in. thickness) polyester barrier from Kapak Corporation of Minneapolis, Minn.). Two of the pouches (pouch U and pouch Y) were filled with about 10 g of a 50/50 mixture of eicosane and pentadecane.

Four chemical packs were formed as in Example 2 using the Kapak material. Each pack was filled with about 75 g deionized water. Immediately before taking measurements, about 50 g of chemical reagent was added to the pack. Pack T was designated as a control pack to which $CaCl_2$ was added. Pack U was designated as an experimental pack to which $CaCl_2$ was added. Pack X was designated as a control pack to which $NH_4NO_3$ was added. Pack Y was an experimental pack to which $NH_4NO_3$ was added.

Figure 15:
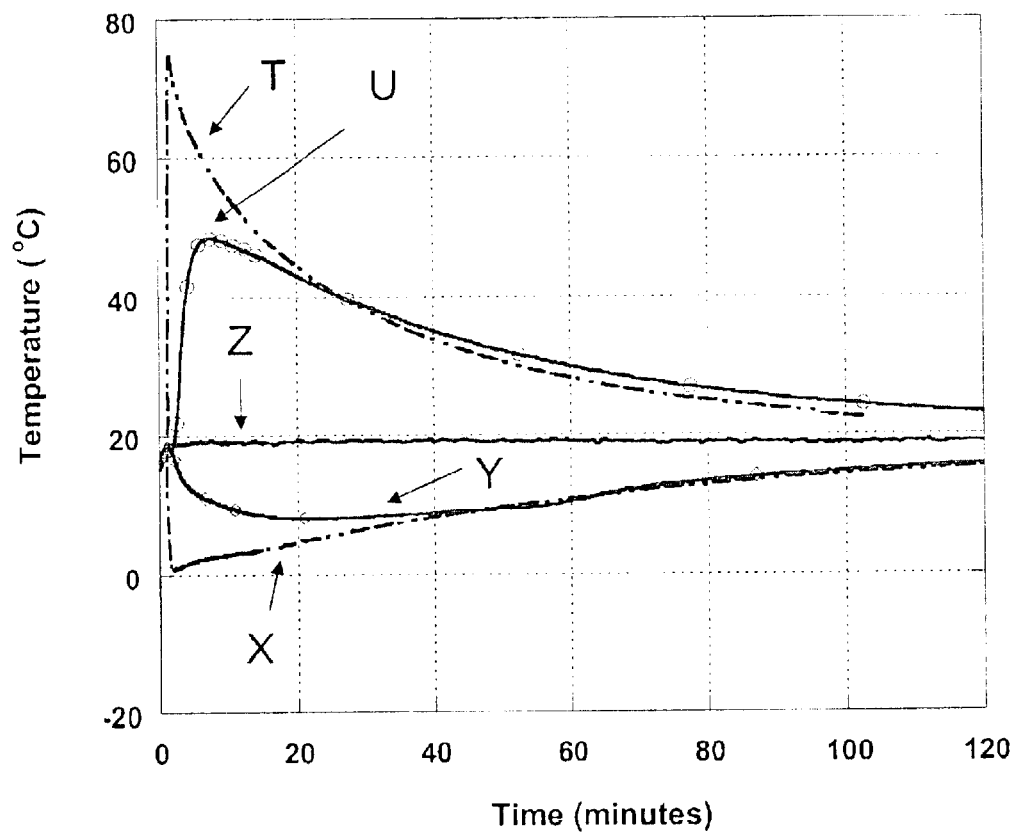
FIG. 15 depicts the temperature as a function of time for various exemplary hot and cold pack systems including no phase change material and a 50/50 mixture of eicosane and pentadecane.

The experimental setup used in FIG. 9 was used to collect time-temperature data for each of the samples. The sample pouch 28 was placed on a test surface 30. The chemical heat pack 32 was placed on top of the sample pouch 28. Polystyrene foam insulation 20 was used to cover the system. Two temperature measurements were taken: $T_1$, the temperature between the bottom surface of the sample pouch and the test surface, and $T_2$, the temperature between the top surface of the sample pouch and the bottom surface of the chemical pack. The data was collected using a DT9805 A/D board (Data Translation) and LabTech Data Acquisition software. The results of the analyses are depicted in FIG. 15. The room temperature over time is depicted as curve Z.

As shown in FIG. 15, the PCM mixture was able to modulate the temperature of both a hot chemical pack (curve U) and a cold chemical pack (curve Y), as compared with the control systems (curve T and curve X, respectively), resulting in a more moderate and longer-lasting temperature profile. The amount and types of PCM's may be modified to optimize the modulation within different temperature ranges.

In summary, the present invention addresses the need for a thermal therapy system that reaches the desired therapeutic temperature, eliminates undesirable temperature spikes, and provides an extended therapeutic duration. By incorporating one or more PCM's into a thermal therapy sleeve, the benefits traditional form of thermal therapy may be enhanced and extended. Further, the thermal therapy system of the present invention may be used to provide a beneficial product combination to the user by providing a thermoactive material, such a chemical pack, a gel-based pack, or a metal oxidation product, and the sleeve into which the material is inserted. This combination is both efficacious and convenient and offers significant benefits over products currently available. Furthermore, the methods contemplated by the present invention offer an array of thermal therapy possibilities for various applications.

The invention may be embodied in other specific forms without departing from the scope and spirit of the inventive characteristics thereof. The present embodiments therefore are to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A flexible thermal therapy sleeve comprising:
   a first layer including a first phase change material having a transition temperature of from about –10° C. to about 40° C.; and
   a second layer including a second phase change material having a transition temperature of from about 35° C. to about 65° C.,
   wherein the first layer is joined to the second layer to form at least a partial enclosure having an opening through which a thermoactive material may be inserted and removed.

2. The sleeve of claim 1, wherein the first phase change material is selected from the group consisting of n-eicosane, n-hemeicosane, n-docosane, n-tricosane, n-tetracosane, n-pentacosane, n-hexacosane, n-heptacosane, n-octacosane, and a combination thereof.

3. The sleeve of claim 1, wherein the second phase change material is selected from the group consisting of n-tridecane, n-tetradecane, n-pentadecane, n-hexadecane, n-heptadecane, n-octadecane, n-nonadecane, n-eicosane, and a combination thereof.

4. A flexible thermal therapy sleeve comprising:
 a first layer including a first phase change material and a second phase change material, the first phase change material having a transition temperature of from about −10° C. to about 40° C. and the second phase change material having a transition temperature of from about 35° C. to about 65° C.; and
 a second layer joined to the first layer to form at least a partial enclosure having an opening through which a thermoactive material may be inserted and removed.

5. The sleeve of claim 1, wherein the first phase change material is selected from the group consisting of n-eicosane, n-hemeicosane, n-docosane, n-tricosane, n-tetracosane, n-pentacosane, n-hexacosane, n-heptacosane, n-octacosane, and a combination thereof.

6. The sleeve of claim 1, wherein the second phase change material is selected from the group consisting of n-tridecane, n-tetradecane, n-pentadecane, n-hexadecane, n-heptadecane, n-octadecane, n-nonadecane, n-eicosane, and a combination thereof.

7. The sleeve of claim 4, wherein the second layer comprises a third phase change material.

8. The sleeve of claim 7, wherein the third phase change material has a transition temperature of from about −10° C. to about 40° C.

9. The sleeve of claim 7, wherein the third phase change material has a transition temperature of from about 35° C. to about 65° C.

10. A thermal therapy system having an extended therapeutic duration comprising:
 a thermoactive material comprising a chemical pack, the pack including a first phase change material, a solute, and a solvent, wherein the solute and the solvent are separated by a membrane, where the rupturing of the membrane causes the combination of the solute and solvent and produces an endothermic reaction or an exothermic reaction; and
 a flexible sleeve including a first layer and a second layer, the first layer including a second phase change material having a transition temperature of from about −10° C. to about 40° C. and a third phase change material having a transition temperature of from about 35° C. to about 65° C.,
 wherein the first layer is joined to the second layer to form at least a partial enclosure having an opening through which the thermoactive material may be inserted and removed.

11. The system of claim 10, wherein the solute comprises ammonium nitrate.

12. The system of claim 10, wherein the first phase change material has a transition temperature of from about −10° C. to about 40° C.

13. The system of claim 10, wherein the first phase change material is selected from the group consisting of n-tridecane, n-tetradecane, n-pentadecane, n-hexadecane, n-heptadecane, n-octadecane, n-nonadecane, n-eicosane, and a combination thereof.

14. The system of claim 10, wherein the solute comprises calcium chloride.

15. The system of claim 10, wherein the first phase change material has a transition temperature of from about 35° C. to about 65° C.

16. The system of claim 10, wherein the first phase change material is selected from the group consisting of n-eicosane, n-hemeicosane, n-docosane, n-tricosane, n-tetracosane, n-pentacosane, n-hexacosane, n-heptacosane, n-octacosane, and a combination thereof.

17. A thermal therapy system having an extended therapeutic duration comprising:
 a thermoactive material comprising a chemical pack, the pack including a first phase change material, a solute, and a solvent, wherein the solute and the solvent are separated by a membrane, where the rupturing of the membrane causes the combination of the solute and solvent and produces an endothermic reaction or an exothermic reaction; and
 a flexible sleeve comprising a first layer and a second layer, the first layer including a second phase change material having a transition temperature of from about −10° C. to about 40° C., and the second layer including a third phase change material having a transition temperature of from about 35° C. to about 65° C.,
 wherein the first layer is joined to the second layer to form at least a partial enclosure having an opening through which the thermoactive material may be inserted and removed.

18. The system of claim 17, wherein the first phase change material has a transition temperature of from about −10° C. to about 40° C.

19. The system of claim 17, wherein the first phase change material has a transition temperature of from about 35° C. to about 65° C.

20. The system of claim 17, wherein the first phase change material, the second phase change material, and the third phase change material are selected from the group consisting of n-eicosane, n-hemeicosane, n-docosane, n-tricosane, n-tetracosane, n-pentacosane, n-hexacosane, n-heptacosane, n-octacosane, n-tridecane, n-tetradecane, n-pentadecane, n-hexadecane, n-heptadecane, n-octadecane, n-nonadecane, n-eicosane, and a combination thereof.

* * * * *